United States Patent [19]

Robey et al.

[11] Patent Number: 5,066,716
[45] Date of Patent: Nov. 19, 1991

[54] SYNTHESIS OF CHLOROACETYL AND BROMOACETYL MODIFIED PEPTIDES FOR THE PREPARATION OF SYNTHETIC PEPTIDE POLYMERS, CONJUGATED PEPTIDES, AND CYCLIC PEPTIDES

[75] Inventors: Frank A. Robey, Bethesda; Raymond L. Fields, Mount Airy, both of Md.; Wolfgang Lindner, Graz, Austria

[73] Assignee: The United States of America as represented by the Secretary of the Department of Health and Human Services, Washington, D.C.

[21] Appl. No.: 283,849

[22] Filed: Dec. 13, 1988

[51] Int. Cl.⁵ ..................... A61K 37/02; C08G 63/44; C08G 63/91; C08G 69/00
[52] U.S. Cl. ............................. 525/54.1; 525/54.11; 528/288; 530/317; 530/335; 530/336; 530/337; 530/345
[58] Field of Search ............... 530/335, 336, 337, 345, 530/317; 528/288; 525/54.1, 54.11

[56] References Cited

PUBLICATIONS

Lindner et al., "Automated Synthesis and Use of N-Chloroacetyl-Modified Peptides for the Preparation of Synthetic Peptide Polymers and Peptide-Protein Immunogenes", Int. J. Peptide Protein Res., 30, 1987, 794–800.

Primary Examiner—Nathan M. Nutter
Attorney, Agent, or Firm—Birch, Stewart, Kolasch & Birch

[57] ABSTRACT

A method to incorporate bromoacetyl and chloroacetyl moieties on amino groups of synthetic peptides using a standard program with an automated peptide synthesizer has been developed. The bromoacetyl and chloroacetyl-derivatized peptides react well with sulfhydryl-containing proteins and with peptides containing cysteine residues. Autopolymerization or cyclization occurs by reaction of the free sulfhydryl of cysteine in a peptide with the bromoacetyl group (or chloroacetyl group) and reactions can generally be controlled by controlling the concentrations of starting peptide in neutral pH buffers. Analytical methods for evaluating the polymers or cyclized peptides include gel filtration chromatography, reverse phase HPLC, SDS-PAGE and amino acid analysis where the degree of reaction can be evaluated by quantifying the amount of S-carboxymethylcysteine formed after HCl hydrolysis. N-bromoacetyl-derivatized peptides are useful as reagents for potential peptide immunogens, vaccines and therapeutics, and for substances such as peptides linked to polymers, plastics, enamels, and ceramics.

22 Claims, 6 Drawing Sheets

5,066,716

SYNTHESIS OF CHLOROACETYL AND BROMOACETYL MODIFIED PEPTIDES FOR THE PREPARATION OF SYNTHETIC PEPTIDE POLYMERS, CONJUGATED PEPTIDES, AND CYCLIC PEPTIDES

FIELD OF THE INVENTION

The present invention relates to the synthesis of chloroacetyl and bromoacetyl modified peptides, and the subsequent preparation of peptide conjugates, polymerized peptides, and cyclized peptides from these bromoacetyl and chloroacetyl modified peptides.

BACKGROUND OF THE INVENTION

Over the past several years, automated peptide synthesizers have become increasingly valuable in biomedical research as a rapid means by which to produce custom-designed peptides for various uses. Most commonly, synthetic peptides are used as immunogens to obtain anti-peptide antibodies which, in turn, are used either to purify native proteins, localize native proteins, or to inhibit the activities of naturally occurring proteins. In general, when raising antibodies is the object, the peptide of interest must first be conjugated to a carrier protein. Although the reasons for this requirement are not clear, the size of the peptide must be a consideration simply because small peptides often do not meet all the criteria necessary for immunogenicity.

The present inventors have been involved in the production of antibodies directed against synthetic peptides and have found it desirable to expand the strategies of peptide-protein chemistry. The peptide synthesizer offers a means of automating insertion of a reactive moiety at a specific position in a synthetic peptide for the purpose of attachment of the peptide to a reactive group on a carrier protein. The automated synthesis of N-chloroacetyl-derivatized peptides was recently reported for this purpose in *Int. J. Peptide Protein Res.* 30, by W. Linder and F. A. Robey, pp. 794–800 (1987). The present invention is an extension of this work in which N-bromoacetyl moieties are also added to the amino termini of synthetic peptides by using standard amino acid coupling chemistry. In addition, several methods are described to produce peptide-protein conjugates, peptide polymers and cyclic peptides.

SUMMARY OF THE INVENTION

An object of the present invention is to provide a method for synthesizing bromoacetyl and chloroacetyl modified peptides.

Another object of the invention is to provide a method for preparing synthetic peptide polymers derived from bromoacetyl and chloroacetyl modified peptides.

Yet another object of the invention is to provide a method for obtaining synthetic cyclized peptides from bromoacetyl and chloroacetyl modified peptides.

Still another object of the invention is to provide a method for producing synthetic peptide conjugates from bromoacetyl and chloroacetyl modified peptides.

A further object of the invention is to produce bromoacetyl and chloroacetyl derivatized proteins which are useful as reagents for potential peptide immunogens, vaccines, and therapeutics.

Another object of the invention is to provide a method to insert a bromoacetyl or chloroacetyl group onto a protected peptide via an amide linkage, so that the bromoacetyl or chloroacetyl group remains after a severe acid hydrolysis used to deprotect the peptide.

Yet another object of the invention is the development of a process of polymerizing or cyclizing bromoacetyl or chloroacetyl derivatized peptides without the production of hazardous by products, and without the need for polymerization initiators or cross linking agents.

These and other objects of the invention are accomplished by providing a method for the preparation of bromoacetyl or chloroacetyl derivatized peptides which comprises the steps of coupling a bromoacetyl or chloroacetyl group onto a fully protected peptide to form an amide linkage between the bromoacetyl or chloroacetyl group and the fully protected peptide, and deprotecting the fully protected peptide while still preserving the presence of the bromoacetyl or chloroacetyl group on the peptide.

The derivatized peptide preferably is an N-bromoacetyl derivatized peptide or an N-chloroacetyl derivatized peptide.

Any peptide can be derivatized using the present method. Preferably, a cysteine-containing peptide or a peptide containing an SH group is utilized as the fully protected peptide if the goal is polymerization or cyclization of the modified peptide.

The N-bromoacetyl or N-chloroacetyl peptides can be prepared by a procedure comprising forming a symmetric anhydride of bromoacetic acid or chloroacetic acid, reacting the bromoacetic acid anhydride or chloroacetic acid anhydride with an N-terminus of a peptide to form an amide linkage, and deprotecting the peptide by treatment with hydrogen fluoride or any other similar acid.

The formation of the symmetric anhydride is conducted at about 0° C. to about 30° C., preferably about 25° C.

The reaction of the bromoacetic acid or chloroacetic acid anhydride with the protected peptide is conducted at about 0° C. to about 30° C., preferably about 25° C.

The treatment with hydrogen fluoride is conducted at about −5° C. to about 5° C., preferably 0° C. This treatment occurs for about 10 minutes to about 3 hours, preferably about 2 hours.

Other similar starting materials, besides bromoacetic acid or chloroacetic acid, can also be used that are sufficient to react with an amino terminus of a fully protected peptide. For example, bromoacetyl bromide and bromoacetyl chloride are appropriate starting materials.

The thus prepared bromoacetyl or chloroacetyl derivatized peptides can be polymerized or cyclized. To be polymerized or cyclized, the derivatized peptide must contain cysteine or any other similar reactive group (having an SH group), or in some cases reactive amines, in the peptide chain.

The polymerization or cyclization can be effected by treating the bromoacetyl or chloroacetyl derivatized peptides in a solution with a pH of about 5 to about 11, preferably about 8. Depending on the particular peptide involved, polymerization or cyclization occurs. Smaller peptides (e.g. having 5 to 6 amino acids) tend to cyclize instead of polymerizing.

The peptides are preferably polymerized or cyclized in a solution of $NaHCO_3$ or $NaHPO_4$ with a pH of about 8, while stirring for about 0.5 to about 48 hours at about +15° C. to 30° C., preferably about 25° C.

Carrier protein-peptide conjugates of the bromoacetyl derivatized or chloroacetyl derivatized peptides are prepared by reacting the derivatized peptides (preferably a derivatized peptide that does not have SH groups or reactive amines) with suitable carrier proteins containing a reactive group such as cysteine or any group with an SH group, and in some cases, reactive amines, so as to form a linkage such as a thio-ether linkage.

The reaction of the derivatized peptide with the carrier protein is conducted for about 0.5 to 48 hours.

The reaction temperature can range from about 15° C. to about 30° C., preferably 25° C.

Suitable carrier proteins that can form conjugates with the bromoacetyl derivatized or chloroacetyl derivatized peptides of the invention include bovine serum albumin, chicken serum albumin, and keyhole lymphet hemocyanin.

The invention also provides bromoacetyl or chloroacetyl derivatized peptides in which the bromoacetyl or chloroacetyl group is bonded to the peptide via an amide linkage, polymers and cyclizates of the derivatized peptides, and conjugates of the derivatized peptides and a carrier protein.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Preparation and stability of N-bromoacetylated peptides

Previously, the present inventors showed that use of the automatic peptide synthesizer is an efficient way for automatic placement of N-chloroacetyl moieties at the N-termini of peptides (Linder, W. and Robey, F. A., Int. J. Peptide Protein Res. 30, pp. 794-800 (1987)). This method of preparation of N-bromoacetyl-derivatized peptides proceeds as well as for N-chloroacetyl peptides in terms of yield and purity. A key advantage of the bromoacetylated peptides over the chloroacetylated peptides is the far greater reactivity of the former toward nucleophilic reagents such as thiols. However, there may be instances in which the chloroacetyl peptides have advantages over the bromoacetyl peptides.

Figure 1:
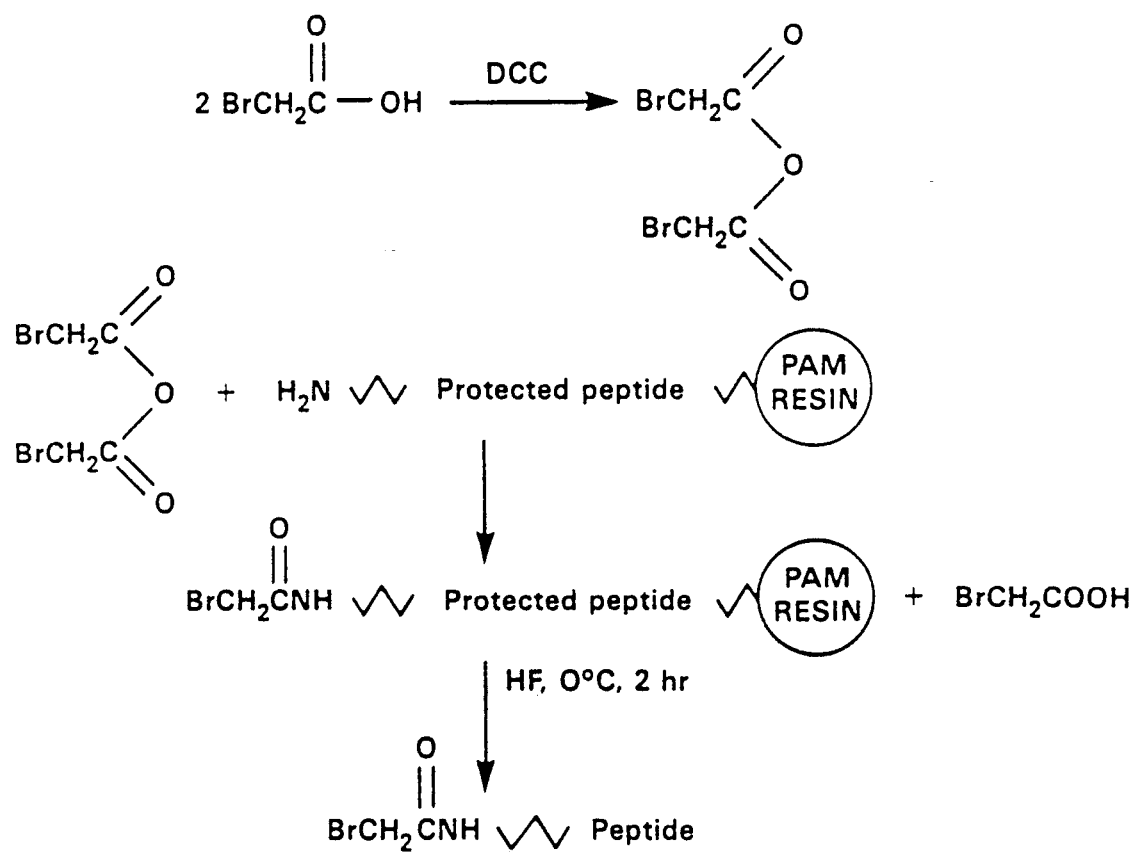
FIG. 1 shows the overall reaction scheme for the formation of the symmetric anhydride of bromoacetic acid and the subsequent reaction of the bromoacetic acid anhydride with the free amine on a PAM (phenylacetamidomethyl) resin to form a bromoacetylated derivatized peptide.

A general reaction scheme for attaching bromoacetyl groups to the amino terminal amine of a peptide is depicted in FIG. 1. All steps are performed by an automated peptide synthesizer, but the reaction can be conducted manually. The symmetric anhydride of bromoacetic acid is first formed by the reaction of bromoacetic acid with DCC (N,N-dicyclohexylcarbodiimide) in $CH_2Cl_2$. The bromoacetic acid anhydride is then reacted with a free amine on the PAM (phenylacetamidomethyl) resin to form the stable amide linkage. Finally, the entire peptide is deprotected and released from the PAM (phenylacetamidomethyl) resin by anhydrous hydrogen fluoride. As in the use of the N-chloroacetyl-derivatized peptides, the bromoacetylated peptides withstand HF treatment used for amino acid side chain deprotection very well. In contrast, attempts to deblock iodoacetylated peptide derivatives by the same HF procedure were unsuccessful. It appears that the iodoacetyl group is unstable to anhydrous HF at around 0° over a time period of 1-2 hours.

Synthesis Examples of N-bromoacetyl peptides

Various N-bromoacetyl peptides were synthesized using an automated solid phase peptide synthesizer (Model 430A, Applied Biosystems, Inc., Foster City, Calif.). As a last step in the synthesis, bromoacetic acid was reacted with the amino terminal amino acid to form a N-bromoacetyl-derivatized fully protected peptide. This procedure was carried out by substituting 2.0 mmol of bromoacetic acid for glycine in an empty glycine cartridge for the last step in the synthesis. Bromoacetic acid anhydride is formed as an intermediate in this reaction. Deprotection and release of the peptide from the PAM resins was accomplished using anhydrous HF with 10% anisole at 0° for 2 hours. Following ethyl acetate extraction of the residual peptide-resin mixture, each peptide was extracted with 0.1M aqueous acetic acid, separated from the resin by filtration through a scintered glass filter and dried by lyophilization. Crude peptides were generally obtained in yields of between 70-90%.

Prior to derivatizing peptides with bromoacetic acid using the automated system, a protected peptide on a PAM resin was bromoacetylated manually using the following procedure: 298 mg bromoacetic acid (2 mmol) in 5 mL $CH_2Cl_2$ was treated with 2 mL of a 0.5M solution of DCC in $CH_2Cl_2$ (1 mmol DCC). The solution was stirred for fifteen min. at 25° C. and during this time a white precipitate of dicyclohexylurea (DCU) formed. The DCU was filtered and the filtrate was evaporated to approximately 2.5 mL using a stream of $N_2$ gas. The volume was adjusted to 6 mL with DMF (dimethylformide) and the solution was further evaporated to approximately 4 mL by bubbling $N_2$ gas into the solution. The initial temperature was 22° C. and evaporation of $CH_2Cl_2$ was carried out with the temperature unadjusted. The solution was then filtered to remove trace amounts of DCU which had formed during the evaporation process.

The protected peptide on resin was synthesized using the automated peptide synthesizer. The t-Boc protecting group was removed from the amino terminus using TFA (trifluoroacetic acid) in $CH_2Cl_2$ followed by neutralization of the resin with diisopropylethylamine as programmed into the standard run file of the instrument by the manufacturer.

To a solution of 0.5 mmol protected peptide (10-mer) on PAM resin in 10 mL DMF was added 4 mL DMF containing 1 mmol bromoacetic acid anhydride (prepared as given above). The reaction was allowed to proceed at 25° C. for 60 min with stirring after which time the reaction appeared to be complete as evidenced by the disappearance of the free amine. The reaction rate was monitored by the ninhydrin reaction of the resin according to the procedure of Sarin et al (Sarin, V. K. et al, *Anal. Biochem.* 117, 147–157 (1981)). The reaction appeared to be greater than 99.8% after 60 min. The resin was then filtered, washed five times with 50 mL aliquots of $CH_2Cl_2$ and air dried.

Deprotection and release of the bromoacetylated peptides from the PAM resins was accomplished by treating the resin with anhydrous HF containing 10% anisole at 0° C. for 2 hr. Following ethyl acetate extraction of the residual peptide-resin mixture, each peptide was extracted with 0.1M aqueous acetic acid, separated from the resin by filtration through a scintered glass filter and dried by lyophilization. Crude peptides were generally obtained in yields of between 70–90%.

The obtained peptides were examined by high performance liquid chromatography (HPLC) using 0.1% TFA/water/acetonitrile gradients and a $C_8$ column. The purity of the peptides ranged from 30–95%. N-bromoacetylated peptides were generally able to be used for the protein-peptide conjugation and/or autopolymerization reactions without further purification. However, when purification was necessary, this was conducted under acidic conditions in order to avoid a reaction between the bromoacetyl group and the thiol groups in the peptides. When there were no thiol groups on the peptide to be purified, the bromoacetyl moiety was stable in aqueous buffers up to one day at 25°. Longer times were not directly investigated nor were the details of how peptide structure might effect the stability of the bromoacetyl moiety. The additional moiety on the deprotected peptide had no effect on the purity of the peptide synthesized prior to addition of the bromoacetyl group.

Amino acid analyses of the N-bromoacetyl peptides were accomplished using a Waters Picotag HPLC system (Millipore Corp., Milford, Mass.). An amino acid standard solution containing S-carboxymethylcysteine was used as the external standard.

Autopolymerization Examples of N-bromoacetylated peptides containing cysteine

The peptide polymers were prepared by dissolving 100 mg of the N-bromoacetyl cysteine-containing peptides in 1.0 mL of deoxygenated 0.5M $NaHCO_3$ or 0.1 M $NaHPO_4$, pH 7.0 buffer and stirring these solutions under $N_2$ for 5–12 hours at 25°. Peptides that were not soluble in aqueous bicarbonate were dissolved in 6M guanidine-hydrochloride in 0.1M $NaHCO_3$. The degree of polymerization was determined by titration of -SH groups with DTNB (5,5'-dithiobis(2-nitrobenzoic acid)) according to a procedure described by G. L. Ellman, *Arch. Biochem. Biophys.* 82. pp. 70–77 (1959), by HPLC gel filtration or by SDS-PAGE (sodium dodecylsulfate polyacrylamide gel electrophoresis) according to the method described by Laemmli, U.K. *Nature* 227, pp. 680–685 (1970), and staining with Coomassie Brilliant Blue.

Cyclization Examples of bromoacetylated peptides

At concentrations considerably less than 100 mg/mL used for the polymerization reaction above, certain bromoacetyl-cysteine-containing peptides tended to cyclize instead of polymerize. Cyclization occurs more readily with some peptides than with others. Presumably, peptide conformation contributes a large influence toward cyclization. In one case, what appeared to be 100% cyclization was obtained at a concentration of peptide of 1 mg/mL in 0.1M $NaHCO_3$. The peptide was highly soluble and the reaction occurred overnight at room temperature.

Cyclic peptides were characterized in a manner similar to that used for the characterization of peptide polymers. In addition, reverse phase HPLC was emphasized in which case the cyclic peptides elute as much as two minutes earlier than their precursors. In addition, it was found that fast atom bombardment mass spectrometry is quite useful in characterizing cyclic peptides.

Synthesis Examples of Carrier Protein-Peptide Conjugates

Conjugates were formed with carrier proteins by first derivatizing the carrier protein with iminothiolane as described in Lindner, W. and Robey, F. A., *Int. J. Peptide Protein Res.* 30. pp. 794–800 (1987), followed by the addition of the bromoacetylated peptide at pH 8.3. Typical reaction conditions were the following: To 30 mg carrier protein (such as BSA-bovine serum albumin; CSA-chicken serum albumin; KLH-keyhole lymphet hemocyanin) dissolved in 2 mL 0.1M $NaHCO_3$ (KLH was dissolved in water first and then brought to 0.1M $NaHCO_3$ by the addition of solid $NaHCO_3$) was added 4 mg of solid iminothiolane. The mixture was stirred for 15 min at room temperature followed by exclusion chromatography on a column ($1.5 \times 10$ cm) containing Sephadex G-25 equilibrated and eluted with 0.1M $NaHCO_3$. To the fractions containing the modified protein (total volume, about 3.5 mL as judged by absorbance readings at 280 nm), the N-bromoacetyl-derivatized peptide (20–50 mg) was added in solid form and the mixture was stirred for 3 hrs at room temperature. The peptide-protein conjugate was obtained following dialysis against 0.1M $NH_4HCO_3$ and lyophilization.

DISCUSSION OF RESULTS

It should be noted that the high reactivity of bromoacetyl moieties may limit the type of scavengers used during the HF deprotection procedure.

Figure 2A:
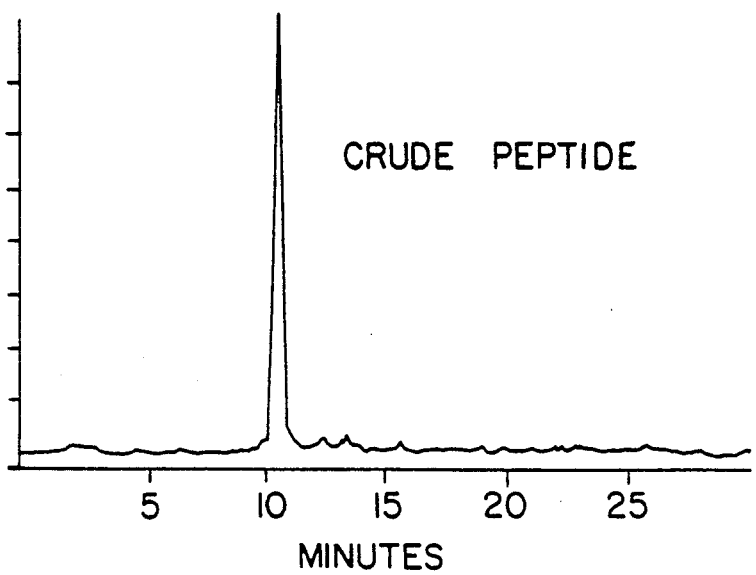
FIGS. 2A and 2B and a chromatographic comparison of a bromoacetylated peptide and the parent peptide.
Figure 2B:
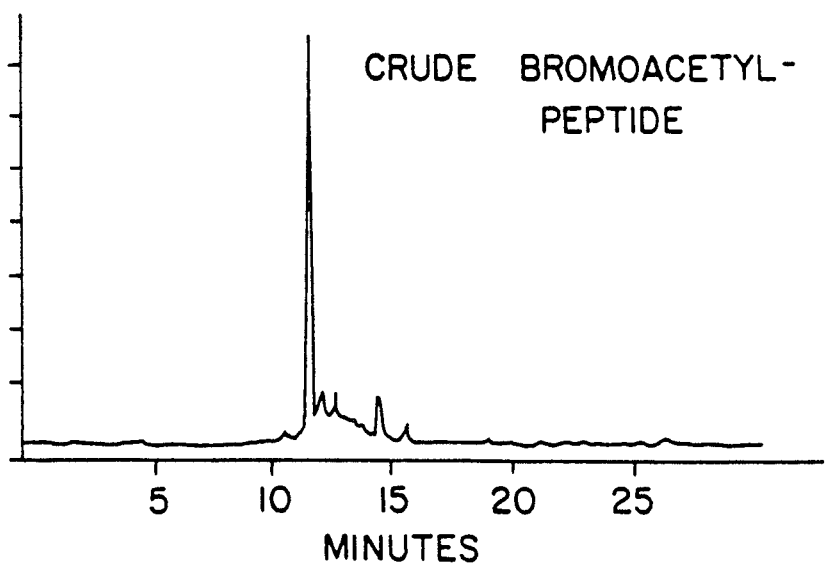

Bromoacetyl peptides were obtained in approximately the same purity as the parent peptides. That is, peptides that were 50% pure were 50% pure after bromoacetylation. An example of this is shown in FIG. 2 in which the crude parent peptide in the top portion is eluted a few seconds earlier than the crude bromoacetylated peptide (bottom) in reverse phase HPLC. The sequence of the peptide used was Lys-Asn-Leu-Lys-Ile-Glu-Asp-Ser-Asp-Thr-Ile-Cys-Glu-Val-Glu-Asp-Glu-Lys-Glu-Glu-Val-$NH_2$. The conditions were the following: Column, $C_8$, Solvent A, 0.1% TFA, Solvent B, 70% acetonitrile in 0.1% TFA. Linear gradient was run from 0–100% B over 30 min.

Figure 3:
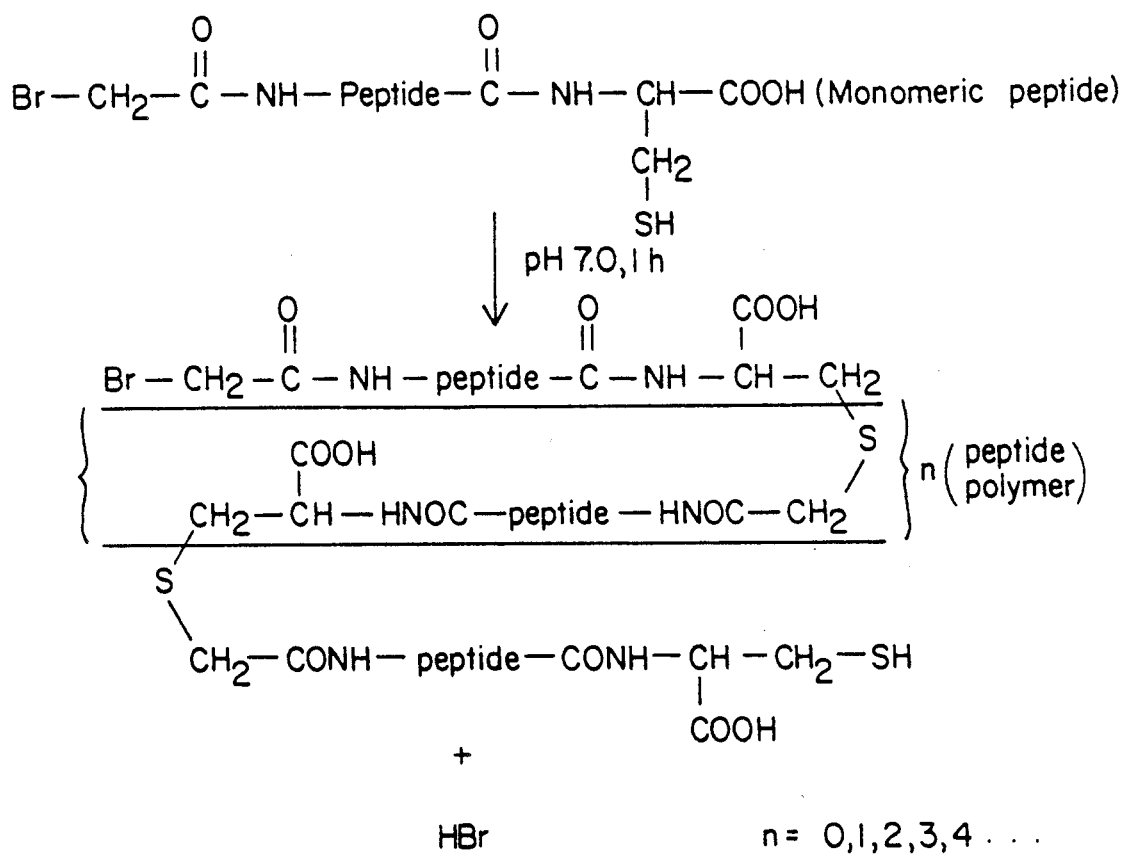
FIG. 3 illustrates the general reaction scheme for the polymerization of peptides by reacting the C-terminal cysteine with the N-terminal bromoacetyl group.
Figure 4:
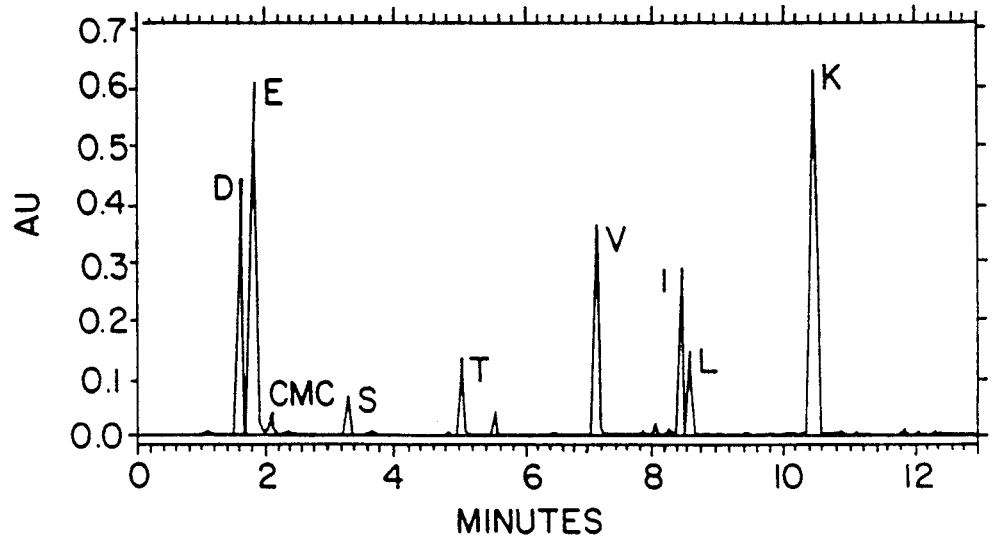
FIG. 4 shows an amino acid analysis (Picotag) of the peptide of FIG. 2 after 5 minutes of polymerization in 0.5M $NaHCO_3$.

The general reaction scheme for the subsequent polymerization reaction is illustrated in FIG. 3. As shown in this figure, cysteine-containing, N-bromoacetyl-derivatized peptides polymerize in most instances in buffers of pH around 7. Polymerization occurs via the stable thio-ether linkage. Hydrolysis of any polymers with 6M HCl at 115° for 22 hrs. liberates stoichiometric amounts of CMC (S-carboxymethylcysteine) which are readily measurable with the Picotag Amino Acid Analysis system, as shown in FIG. 4.

Figure 5A:
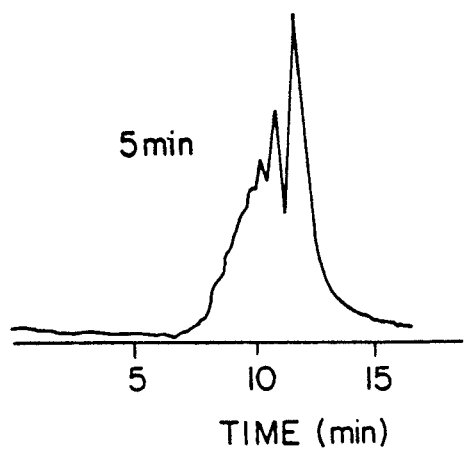
FIGS. 5A, 5B and 5C depict gel filtration HPLC examination of the polymerization of the peptide of FIG. 2.
Figure 5B:
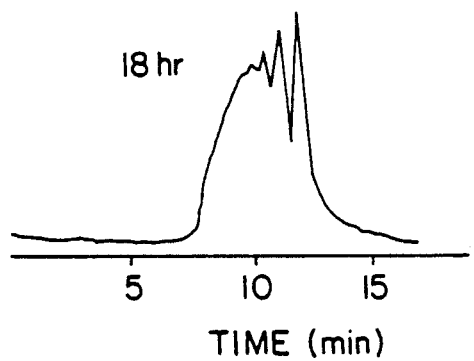
Figure 5C:
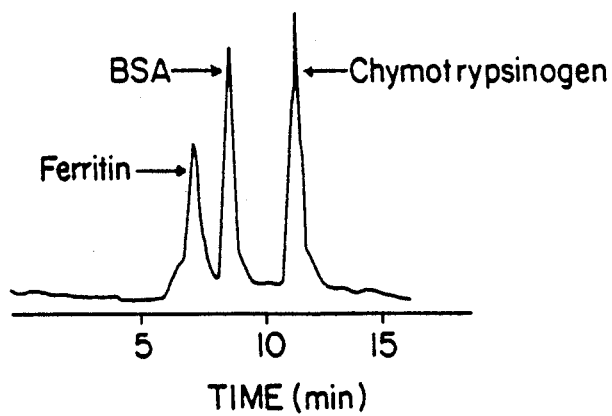

In addition to determining the degree of polymerization by measurement of CMC formed upon HCl hydrolysis, polymerization can also be followed by gel filtration chromatography, SDS-PAGE and/or by reverse phase HPLC. An example of visualization of a polymerization reaction by gel filtration chromatography is given in FIG. 5. The molecular weight standards shown in panel C are ferritin, M.W., 450,000; BSA, 67,000; chymotrypsinogen, 25,000. The column used is the DuPont GF-250, buffer is 0.01M $Na_2HPO_4$, and flow rate is 1.0 mL/min.

On SDS-PAGE (sodium dodecylsulfate polyacrylamide gel electrophoresis) using 13% gels, the polymerized peptide appears as a smear covering the entire lane. Reverse phase HPLC of the polymer produces broad unresolved peaks eluting several minutes after the nonpolymerized peptide. The behavior noticed for the polymer on reverse phase HPLC strongly suggests that the polymers have unique structures not found in the monomeric peptides.

The present inventors have noticed that sometimes the peptides fail to polymerize. It has been observed that when a peptide does not detectably polymerize under these conditions, cyclization has occurred. In one instance it was the formation of small cyclic dimers and trimers that was noticed.

Figure 6A:
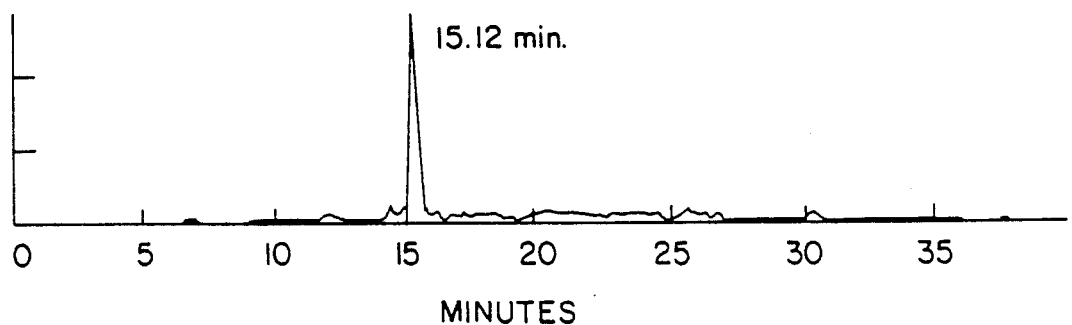
FIGS. 6A and 6B show reverse phase HPLC of bromoacetyl-YIGSRC-$NH_2$, panel A, and cyclic YIGSRC-$NH_2$, panel B.
Figure 6B:
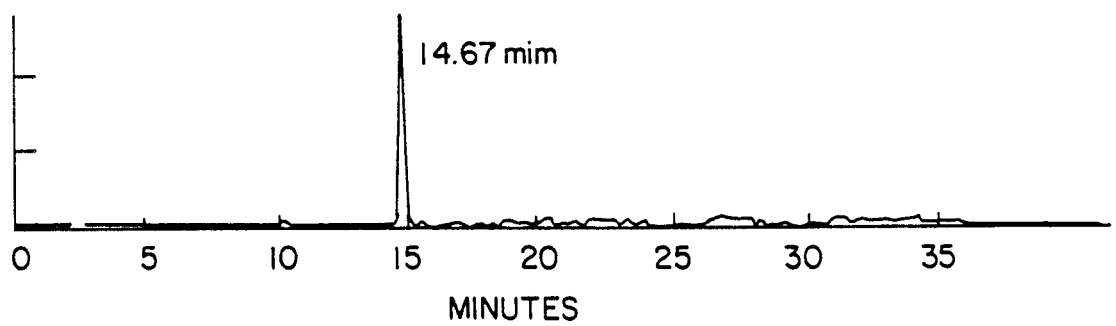

An example of spontaneous cyclization of a peptide using the present methodology is shown for Tyr-Ile-Gly-Ser-Arg (YIGSR), a pentapeptide believed to be a cell attachment site of the connective tissue protein, laminin (Graf, J., Iwamoto, Y., Sasaki, M., Martin, G. R., Kleinman, H. K., Robey, F. A., and Yamada, Y. (1987) Cell 48, pp. 989–996) and reported to have potent antimetastatic activity for certain metastasizing cell lines (Iwamoto, Y., Robey, F. A., Graf, J., Sasaki, M., Kleinman, H. K., Yamada, Y., and Martin, G. R. (1987) Science 238, pp. 1132–1134). When bromoacetyl-YIGSR-Cys-$NH_2$ is placed into a buffer at pH 7 or 8, there is a rapid decrease in free sulfhydryl groups and a shift to an earlier retention time during reverse phase HPLC. This is shown in FIG. 6, in which the cyclized material eluted from the $C_8$ column 0.45 min earlier than the noncyclized peptide. The conditions of the HPLC are the same as in FIG. 2. The cyclized material elutes about 0.45 minutes earlier than the uncyclized precursor.

Figure 7:
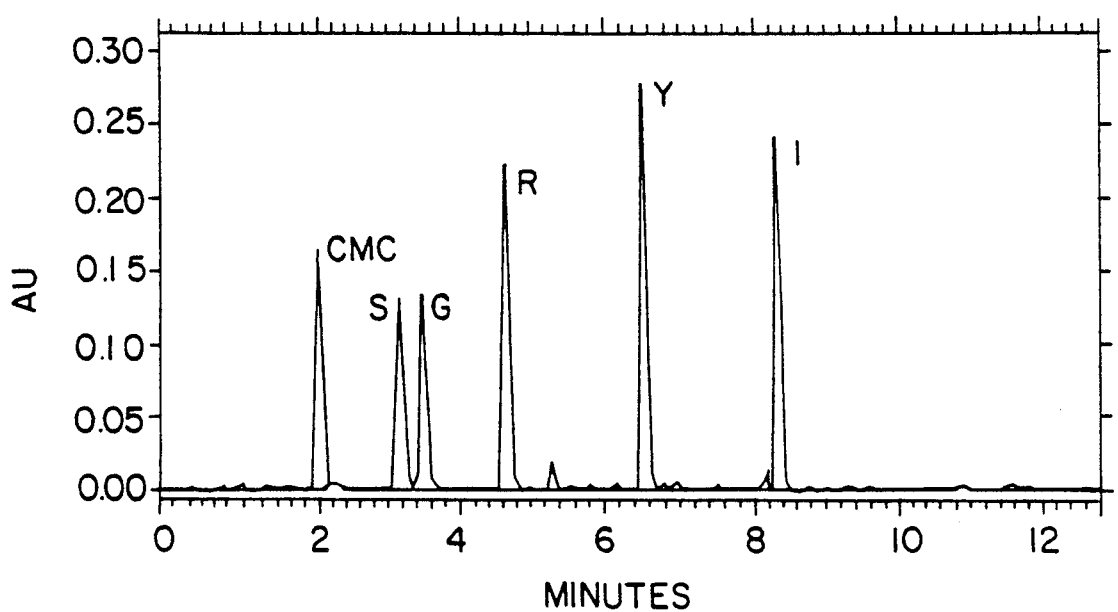
FIG. 7 illustrates an amino acid analysis (Picotag) of cyclic YIGSRC-$NH_2$.

Elution from the HPLC columns earlier than the parent peptide derivatives seems to be a general property of cyclized peptides. The reasons for this may be the decreased hydrophobic surface area of the cyclized peptide. Consistent with the cyclization of bromoacetyl-YIGSRC-$NH_2$ is the stoichiometric value for CMC (FIG. 7) in the acid hydrolysate of the cyclic YIGSR.

Preliminary studies have shown that the cyclized YIGSR is at least 2-times more active than noncyclized YIGSR in blocking the metastases of certain tumor cell lines.

Synthesis of N-chloroacetyl peptides

Various N-chloroacetyl-derivatized peptides were synthesized using an automated solid phase peptide synthesizer (Model 430A, Applied Biosystems, Inc., Foster City, Calif.). In addition to the predetermined amino acid sequence of the desired peptide, N-chloroacetylglycylglycine was incorporated at the N-terminus using the following conditions for automation: 2.0 mmol N-chloroacetylglycylglycine per 0.5 mmol preceding peptide was added to each of 2 blank synthesizer amino acid cartridges and the instrument was programmed to perform the same double coupling procedure as that which is used to couple arginine to a peptide. Because of the N-chloroacetyl-amino acids and N-chloroacetylglycylglycine are soluble in DMF, the coupling of the N-chloroacetylglycylglycine and other N-chloroacetyl-amino acids to the N-terminal amino acid were performed via the active ester formation using DCC with HOBT (hydroxybenzotriazole) in DMF.

The cysteine moiety in the cysteinyl peptides was either placed at the C-terminus or directly after the chloroacetylglycylglycine at the N-terminus. Thus, polymerization of the peptides could be performed by either head-to-tail polymerization (cysteine near C-terminus) or head-to-head polymerization (cysteine near N terminus). Deprotection and release of the peptides from the PAM resins was accomplished using anhydrous HF with 10% anisole or thioanisole at 0° for 2 hours. Following ethylacetate treatment of the residual peptide-resin mixture, the peptides were extracted with 0.1M aqueous acetic acid and separated from the resin. After lyophilization of the aqueous solution the crude peptides were obtained in yields of between 70 and 90%. The purity of the peptides was usually examined by HPLC analysis using 0.1% TFA-water acetonitrile gradients and a $C_8$-column and the purity of the peptides ranged from 80 to 95%. The N-chloroacetyl peptides are generally used without further purification for the protein peptide conjugation and/or autopolymerization reactions. Amino acid analysis of the peptide N-acetylcysteinyl peptide polymers were accomplished using the Waters Pico Tag HPLC system (Millipore Corp., Milford, Mass.). An amino acid standard solution containing S-carboxymethylcysteine (Pierce Chemicals) was used as an external standard.

Autopolymerization of N-chloroacetyl peptides Containing Cysteine

Peptide polymers were formed by dissolving 30 mg N-chloroacetyl cysteinyl peptide in 5 mL of 0.1M $NaHCO_3$ and stirring this solution for 5–12 hours at room temperature. The pH of the solution was occasionally checked and maintained at pH 7.5 to 8.0 by adding solid $NaHCO_3$ if necessary. Peptides which were only slightly soluble in aqueous bicarbonate were dissolved in 6M guanidine-HCl followed by pH adjustment to 7.5–8.0 with ammonia.

The endpoint of the polymerization reaction (diminishing of free SH groups) was determined by the Ellman's reaction (Ellman, G. L. (1959) Arch. Biochem. Biophys. 82. pp. 70–77). The resulting peptide polymerization solution was dialyzed against water or 0.5% acetic acid and subsequently hydrolyzed as described above. The molecular weight cut-off of the dialysis tubing was 1500, 3500, and 6000–8000, respectively, depending on the degree of polymerization of the main fraction. The yield of product based on weight after dialysis and lyophilization varied between 30 and 80%.

The characterization of the dried peptide polymers was carried out using SDS-PAGE according to Laemmli (Laemmli, U.K. (1970) Nature 227, pp. 680–685). Based on the numbers of bands and the molecular weight cut-off of the dialysis tubing the degree of polymerization of the desired product could be evaluated and controlled. The gels were stained with Coomassie blue, and some peptide polymers were not detectable under standard conditions for unknown reasons (leaching out of the gel could be possible).

The characterization via HPLC using a GPC type column (GF-250, DuPont, Wilmington, Del.) showed that, in principle, a Gaussian-type molecular weight distribution is observed, but the resolution of this column was not sufficient to separate the particular units from each other.

Hydrolysis of the peptide polymer followed by amino acid analysis using the Waters Pico Tag system proved that the chemical structure of the peptide monomer was correct and that alkylation of the sulfhydryl group occurs as indicated by the presence of S-carboxymethylcysteine.

Preparation of Carrier Protein-Peptide Conjugates

Conjugates were formed by adding the solid N-chloroacetyl peptide directly to a freshly prepared solution of an iminothiolane-modified carrier protein using the Traut's reagent. Prior to the peptide conjugation reaction, the excess of the reagent was removed from the protein by gel filtration using Sephadex G-10 or G-25. Typical reaction conditions were the following: 30 mg carrier protein (BSA or CSA or KLH) were dissolved in 2 mL 0.1M NaHCO$_3$ (pH 8.0). To this solution 4 mg solid iminothiolane (Traut's reagent) was added and stirred for 15 minutes at room temperature followed by chromatographic separation on a column (1.5 × 10cm) containing Sephadex G-25 equilibrated and eluted with 0.1M NaHCO$_3$. To the fractions containing the modified protein (total volume, about 3.5 mL), as judged by absorbance readings at 280 nm, the N-chloroacetyl-derivatized peptide (10$^{-2}$M corresponding to about 20–50 mg peptide, depending on its molecular weight) was added in solid form and stirred for 3 hours at room temperature. The pH was often adjusted to between 7.5 and 8.0 using solid NaHCO$_3$.

There are several other potential uses of the present chloro and bromo acetylated peptides which have not yet been fully explored. Conceptually, any nucleophile should be capable of displacing the bromide or the chloride from these peptides to form strong covalent linkages and the uses could range from enzyme active site modifications to the attachment of peptides to inert polymers or ceramics, or other substances. Recently, an alternate method of polymerization was reported for the preparation of peptide polymers for use as possible immunogens (See Posnett, D. N., McGrath, H. and Tam, J. P., *J. Biol. Chem.*, 263pp. 1719–1725 (1988)).

Any final products made using the present bromo or chloro acetyl peptides as starting materials in the synthesis or manufacture of the product are included within the scope of the claimed invention.

The invention being thus described it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for the preparation of bromoacetyl or chloroacetyl derivatized peptides, which comprises the steps of:

coupling a bromoacetyl or chloroacetyl group onto a fully protected peptide to form an amide linkage between said bromoacetyl or chloroacetyl group and said fully protected peptide; and deprotecting said fully protected peptide while still preserving the presence of said bromoacetyl or chloroacetyl group on said peptide.

2. The method according to claim 1, wherein said derivatized peptide is an N-bromoacetyl derivatized peptide.

3. The method according to claim 1, wherein said derivatized peptide is an N-chloroacetyl derivatized peptide.

4. The method according to claim 1, wherein said fully protected peptide contains cysteine, a group with an SH group, or a reactive amino group in the peptide chain.

5. The method according to claim 1, which comprises forming a symmetric anhydride of bromoacetic acid or chloroacetic acid; reacting said bromoacetic anhydride or chloroacetic acid anhydride with an N-terminus of a protected peptide to form said amide linkage; and deprotecting said peptide by treatment with an acid.

6. The method according to claim 5, wherein the formation of said symmetric anhydride of bromoacetic acid or chloroacetic acid occurs at about 0° C. to about 30° C.

7. The method according to claim 5, wherein the reaction of the bromoacetic acid and anhydride or chloroacetic acid anhydride with the protected peptide is conducted at about 0° C. to about 30° C.

8. The method according to claim 5, wherein the treatment with the acid is conducted at about −5° C. to about 5° C.

9. The method according to claim 8, wherein the treatment with the acid is conducted for about 10 minutes to about 3 hours.

10. A method according to claim 4, which further comprises polymerizing or cyclizing said bromoacetyl or chloroacetyl derivatized peptide by treating said derivatized peptide in a solution having a pH of about 5 to about 11.

11. The method according to claim 10, wherein said polymerization or cyclization occurs in a solution of NaHCO$_3$ or NaHPO$_4$ having a pH of about 8.

12. The method according to claim 11, which is conducted at about 15° C. to about 30° C.

13. The method according to claim 12, which is conducted for about 0.5 to about 48 hours.

14. The method according to claim 1, which further comprises reacting the bromoacetyl or chloroacetyl derivatized peptide with a carrier protein containing cysteine, a group having an SH group, or a reactive amine to form a conjugate.

15. The method according to claim 14, wherein the reaction is conducted for about 0.5 hours to about 48 hours at a temperature of about 15° C. to about 30° C.

16. The method according to claim 14, wherein said carrier protein is a member selected from the group consisting of bovine serum albumin, chicken serum albumin, and keyhole lymphet hemocyanin.

17. A bromoacetyl or chloroacetyl derivatized peptide in which the bromoacetyl group or chloroacetyl group is bonded to the peptide via an amide linkage.

18. A polymer of the derivatized peptide of claim 17.

19. A cyclized form of the derivatized peptide of claim 18.

20. A conjugate of a carrier protein and the derivatized peptide of claim 17.

21. A method for the preparation of bromoacetyl or chloroacetyl derivatized proteins, which comprises:
coupling a bromoacetyl or chloroacetyl group onto a fully protected peptide at a pH of about 5 to about 11 for about 10 minutes to about 48 hours at about −5° C. to 30° C. in an aprotic polar solvent to form an amide linkage between said bromoacetyl or chloroacetyl group and said fully protected peptide, and deprotecting said fully protected peptide while still preserving the presence of said bromoacetyl or chloroacetyl group on said peptide at a temperature of about −5° C. to about 5° C. for about 10 minutes to about 3 hours in trifluoroacetic acid or hydrogen fluoride.

22. A peptide carrier conjugate produced by a process which comprises reacting the derivatized peptide of claim 17 with a carrier selected from the group consisting of polymers, enamels and ceramics.

* * * * *